United States Patent [19]
Yazaki

[11] Patent Number: 5,755,381
[45] Date of Patent: May 26, 1998

[54] AROMA EMISSION DEVICE

[76] Inventor: Seiichi Yazaki, 13-3-2305, Nakanocho 5-Chome, Miyakojima-ku, Osaka, Japan

[21] Appl. No.: 749,566

[22] Filed: Nov. 15, 1996

[30] Foreign Application Priority Data

Nov. 17, 1995 [JP] Japan ................ 7-335627

[51] Int. Cl.$^6$ .............. A24F 25/00; A61L 9/04; B01D 47/02
[52] U.S. Cl. ............. 239/43; 239/59; 261/121.1; 261/DIG. 65
[58] Field of Search ................. 239/34, 37, 39, 239/42, 43, 57, 58, 59; 261/121.1, DIG. 65

[56] References Cited

U.S. PATENT DOCUMENTS

| | | | |
|---|---|---|---|
| 917,151 | 4/1909 | Rich | 239/40 |
| 1,579,111 | 3/1926 | Hinkson | 239/34 |
| 2,670,236 | 2/1954 | Bradburn | 239/34 |
| 4,226,829 | 10/1980 | Mike | 261/DIG. 65 X |

Primary Examiner—Andres Kashnikow
Assistant Examiner—Robin O. Evans
Attorney, Agent, or Firm—Thompson Hine & Flory LLP

[57] ABSTRACT

An aroma emission device for emitting aroma from an aromatic liquid such as a perfume and eau de Cologne for a certain period of time at a uniform level of aroma without using gas, heat, electricity or any other energy source. The vessel of the device is constructed of an upper compartment and a lower compartment with a partitioning plate therebetween. The upper and lower compartments have respective top and bottom cover portions through which respective air tubes are allowed to pass. Each air tube is open to the outside while its inner open end open deep inside each compartment. A perforation is provided in the partitioning plate to allow the upper compartment to communicate with the lower compartment. By simply alternating the vessel upside down and up, vaporized aromatic liquid is given off and spread out.

4 Claims, 4 Drawing Sheets

AROMA EMISSION DEVICE

BACKGROUND OF THE INVENTION

1. Field of the Invention

The present invention relates to an aromatizer.

2. Description of the Related Art

Aromatics today find widespread use, ranging from toilet deodorizing purposes to aromatizing homes, reception rooms of offices and even cars. Conventional aromatic emission devices spray in aerosols an aromatic contained in a vessel of the device, heat an aromatic to evaporate it, or give off aroma by employing electric or mechanical means. All of them consumes energy in one form or another for giving off aroma.

Daily experience shows that we human beings quickly become insensitive to an aroma, even if it is an excellent quality aroma, when the aroma is continuously inhaled.

Continuous exposure of the mucosa of the nostril to a stimulant causes the sense of smell to be paralyzed.

Optimum emission quantity and time of an aroma is naturally determined by an intended space. An aroma emission time of 2–3 minutes at a time is generally accepted as preferable. When aroma is given off in gaseous form, by heating, or by electric or mechanical means, as described above, its heat source must be switched off and the device must be closed from the atmosphere by a cover to suspend aroma emission. If the timing of suspension is not properly set, the aromatic becomes pungent and the operation of the device is not economical.

SUMMARY OF THE INVENTION

Accordingly, it is an object of the present invention to provide an aroma emission device which finds application for toilet deodorizing purposes and for aromatizing homes, offices and cars, and which functions as an interior decoration. It is another object of the present invention to provide an aroma emission device that gives off aroma at its uniform level for a fixed period of time without using gas, heat, electric and mechanical means. It is yet another object of the present invention to provide an aroma emission device that is repeatedly used simply by placing the vessel of-the device upside down any time.

To achieve the above objects, the present invention comprises a vessel that is partitioned into an upper compartment and a lower compartment, having a top cover portion and a bottom cover portion, respectively, each of the cover portions has an air tube penetrating therethrough for communicating with the atmosphere, the inner open end of each air tube is positioned near a partitioning plate between both compartments, and a perforation is arranged in the partitioning plate to allow the upper and lower compartments to communicate with each other. According to the above arrangement, as air is let into the upper compartment through the air tube (functioning as an air inlet tube), an aromatic liquid held in the upper compartment, by the volume of air taken in, flows down through the perforation into the partitioning plate. Along with the flow of the aromatic liquid, evaporated aromatic liquid builds up in the empty portion of the bottom compartment. The liquid level in the bottom compartment rises while aroma is given off through the air tube (functioning as an air outlet tube) of the lower compartment. Thus, aroma spreads into the interior of a room. When the aromatic liquid in the upper compartment fully transfers into the lower compartment, the emission of aroma-laden air stops. By placing the vessel of the device upside down, the emission of aroma is repeated again.

DESCRIPTION OF THE PREFERRED EMBODIMENTS

Figure 1:
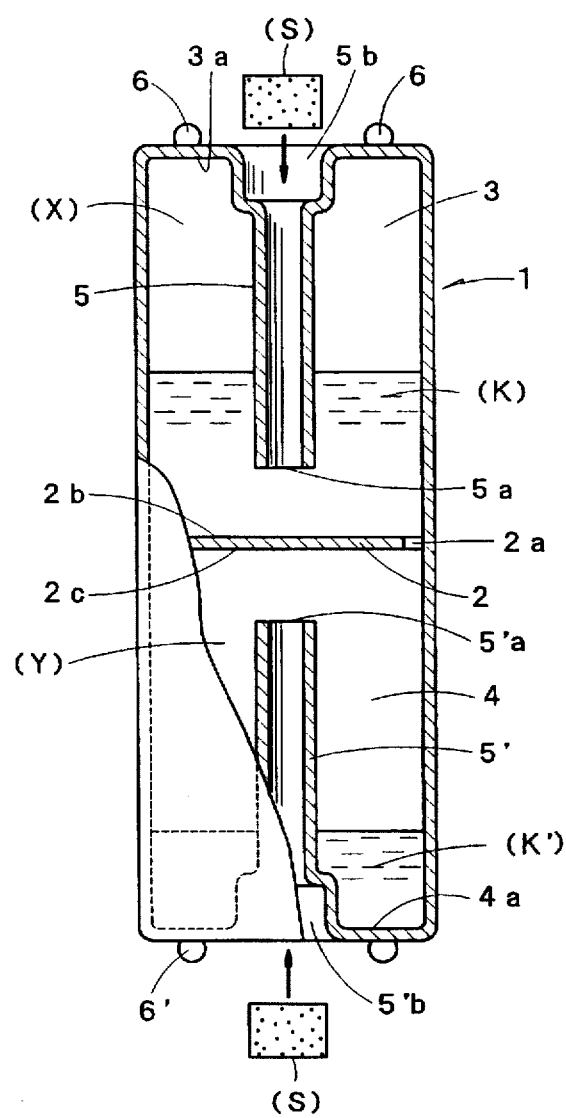
FIG. 1 is a fragmentary front view showing generally the vessel of the device.

Referring now to the drawings, the embodiments of the present invention are now discussed.

FIG. 1 shows one embodiment of the present invention. A vessel 1 of the device of the present invention has a cylindrical form with a predetermined height and predetermined diameter. Preferably, the vessel 1 is integrally formed of transparent glass or transparent hard plastic material. The vessel 1 is divided by a partitioning plate 2 perpendicular to and in the middle of the axis of the vessel 1, into an upper and lower compartments 3, 4. The partitioning plate 2 is provided with one or more perforations 2a for allowing both compartments 3 and 4 to communicate with each other. An air tube 5 extends downward from the center of the top cover portion 3a of the upper compartment 3 with its inner open end 5a coming close to the top surface 2b of the partitioning plate 2. The air tube 5 allows the interior of the upper compartment 3 to communicate with the atmosphere outside.

The lower compartment 4 of the vessel 1 has a same construction as that of the upper compartment 3. The upper-compartment 3 and the lower compartment 4 are symmetrical with respect to the partitioning plate 2. Namely, an air tube 5' extends upward from the center of the bottom cover portion 4a of the bottom compartment 4 with its inner open end 5'a coming close to the bottom surface 2c of the partitioning plate 2. The air tube 5' allows the interior of the lower compartment 4 to freely communicate with the atmosphere outside.

The outside surfaces of the top and bottom cover portions 3a, 4a of the top and bottom compartments 3, 4 may be, for example, flat, wavy or semispherical or of any configuration that may be good in the standpoint of design. Feet 6, 6' are provided as necessary to assure the flow of air through the end openings 5b, 5'b of the air tubes 5, 5' even when the vessel 1 is placed upside down. Optionally, open-cell type sponges (S) may be fitted into the end openings 5b, 5'b of the air tubes to control the flow of air into and out of the compartments.

Desired gaps (clearances) between the inner open ends 5a, 5'a of the air tubes 5, 5' and the top and bottom surfaces 2b, 2c of the partitioning plate 2 are set such that each of the inner open ends is above the maximum level of the aromatic liquid (K) in each of the compartments. Within this limitation, the gaps are set to be as wide as possible. The reason for this is now discussed referring to the state in FIG. 1. When the aromatic liquid (K) held in the upper compartment 3 flows down through the perforation 2a into the lower compartment 4, the inner air contained between the bottom surface 3a of the top cover portion and the liquid level in the upper compartment 3 goes negative in pressure along with the drop of the liquid level. This helps slow the flowing of the aromatic liquid (K). When the aromatic liquid (K) in the upper compartment 3 is fully transferred into the lower compartment 4, the overflowing of the aromatic liquid above the inner open end 5'a in the lower compartment 4 must be prevented.

For simplicity, suppose that a certain amount of aromatic liquid (K) is held in the upper compartment 3 of the vessel 1 that is now in its normal position as shown in FIG. 1. Air is introduced through the end opening 5b and the inner open end 5a of the air tube 5, is then raised through the liquid in bubbles joins the inner air (X) in the upper compartment 3, and then pressurizes the liquid level, causing the aromatic liquid (K) in the upper compartment 3 to flow down into the lower compartment 4 through the perforation 2a in the partitioning plate 2. The amount of liquid flow balances the volume of air taken in through the air tube 5 into the upper compartment 3. Along the transfer of the aromatic liquid, the aroma of the liquid is vaporized and the vaporized aroma fills the top space in the lower compartment 4. With its level rising, the aromatic liquid (K') in the lower compartment 4 pushes up the aroma-laden air (Y), pressurizing the air. The aroma-laden air is thus continuously discharged through the inner open end 5'a and the end opening 5'b of the air tube 5' into the atmosphere. The atmosphere in the room is thus aromatized. To introduce the aromatic liquid (K) into the upper compartment 3, the vessel 1 in FIG. 1 is placed upside down, and a desired aromatic liquid is dropped into the lower compartment 4 through the end opening 5'b of the air tube 5' using a dropping pippete. The aromatic liquid (K) flows through the perforation 2a in the partitioning plate 2 and is stored in the upper compartment 3 that is now positioned down. It is important that the amount of the aromatic liquid introduced is determined such that the level of the aromatic liquid stays below the inner open end 5a of the air tube 5 in the upper compartment 3. The vessel 1 is now put back into its normal position as shown in FIG. 1. This completes the filling of the upper compartment 3 with the aromatic liquid (K).

Figure 2:
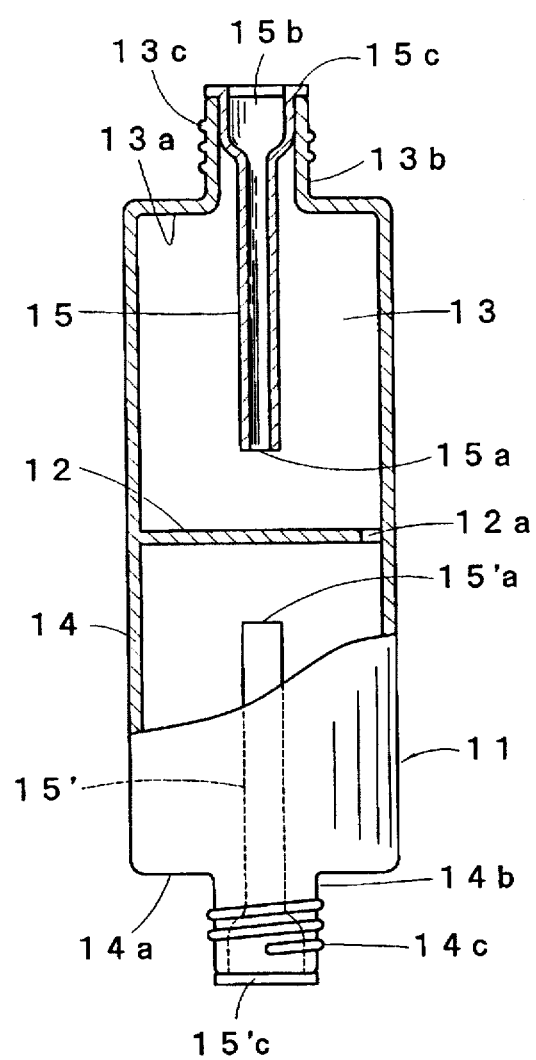
FIG. 2 is a fragmentary front view of another embodiment of the present invention.

FIG. 2 shows the vessel in another embodiment of the aroma emission device of the present invention. The principle of aroma emission remains unchanged from that for the first embodiment. The vessel 11 has a cylindrical form of transparent plastic with predetermined length and diameter. The interior of the vessel 11 is divided by a partitioning plate 12 perpendicular to and in the middle of the axis of the vessel 11, into an upper and lower compartments 13, 14. The partitioning plate 12 has, in its periphery portion, one or more perforations 12a for allowing both compartments 13 and 14 to communicate with each other.

Figure 3:
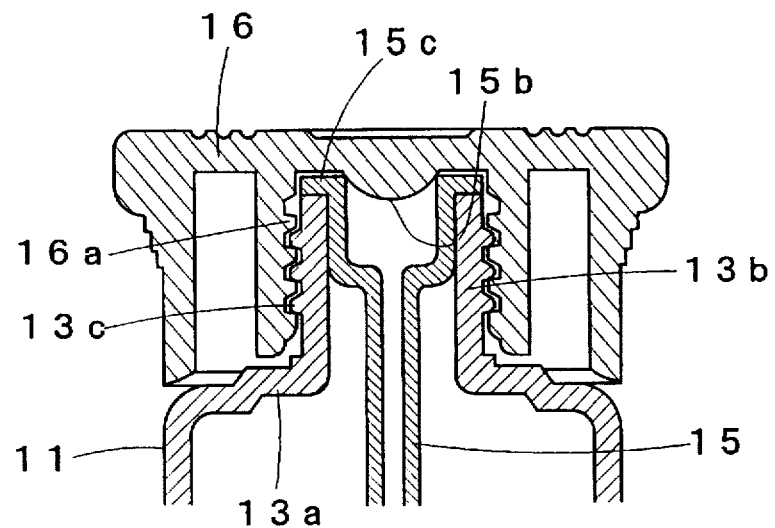
FIG. 3 is an enlarged cross-sectional view showing part of a lid that is tightened around the projected opening of the upper compartment of the vessel of the device.
Figure 4:
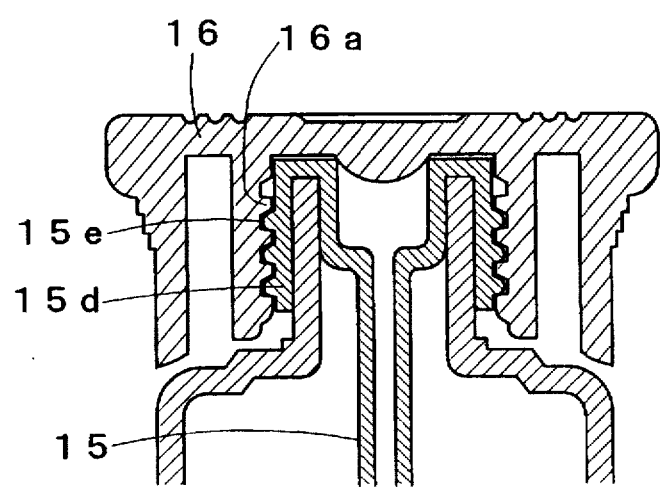
FIG. 4 is a fragmentary enlarged cross-sectional view of another embodiment of the lid.

The vessel 11 has hollow projections 13b, 14b that extend from the centers of the top cover portion 13a and bottom cover portion 14a, respectively. Each of the projections 13b, 14b have on their respective outer circumferences, threads 13c, 14c, around which lids 16 to be described later are screwed. Separately produced air tubes 15, 15' are inserted into the openings of the projections 13b, 14b until the inner open ends 15a, 15'a come close to the partitioning plate 12. FIG. 3 is the enlarged cross-sectional view showing the female thread 16a of the lid 16 that is screwed around the thread 13c of the projection 13b of the upper compartment 13 in the vessel 11 in FIG. 2. By loosening the screwed lid 16 to an appropriate extent, the end opening 15b of the air tube 15 is opened to control appropriately the amount of introduced air. FIG. 4 is the fragmentary enlarged cross-sectional view showing another embodiment of the lid 16. In FIG. 3, the thread 13c is formed on the outer circumference of the projection 13b on the vessel 11. The top flange 15c of the air tube 15 is engaged with the end of the projection 13b. In FIG. 4, no thread is formed on the outer circumference on the projected top 13b on the vessel 11. The top end of the air tube 15 is folded back downward to form an outer sleeve portion 15d so that the projection 13b is sandwiched between the air tube 15 and its outer sleeve portion 15d. Formed on the circumference of the outer sleeve portion 15d is a thread 15e which is engaged with the female thread 16a of the lid 16.

Figure 5:
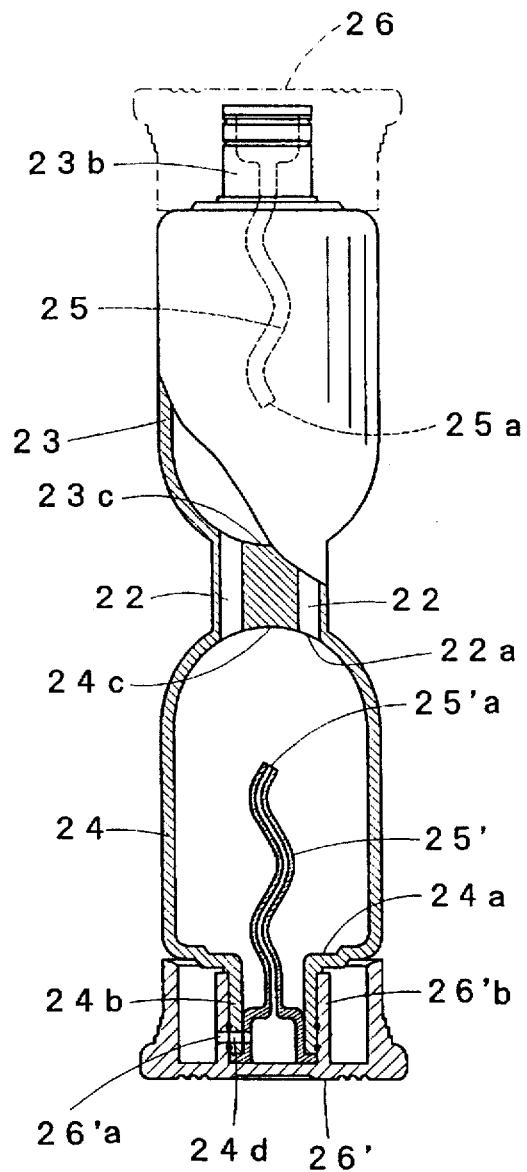
FIG. 5 is a fragmentary front view showing another embodiment of the present invention.

FIG. 5 shows another embodiment of the vessel of the device. Unlike the preceding embodiments, the vessel 21 is non-cylindrical. Its upper compartment 23 and lower compartment 24 are separately formed. Hollow projections 23b, 24b coaxially extend from top and bottom cover portions 23a, 24a, respectively. Air tubes 25, 25' are fitted into the respective projections 23b, 24b and secured such that the inner open ends 25a, 25'a of the air tubes 25, 25' are close to the bottom surfaces 23c, 24c of the respective compartments. Through-holes 23d, 24d, round or horizontally elongated in cross section, are drilled through the end portions of the air tubes 25, 25' and the projection 23b, 24b, respectively. The upper and lower compartments 23, 24 thus constructed are substantially identical in shape, and are connected together with the bottom faces 23c, 24c facing each other. The upper and lower compartments communicate with each other through one or more small passages 22 through both bottom surfaces.

In this case, it is necessary to avoid positioning the inner open ends 25a, 25'a to the openings 22a of the passage 22 in a face-to-face fashion. When the aromatic liquid in the upper compartment 23 or lower compartment 24 drops into the lower compartment 24 or upper compartment 23 through the small passage 22, flow of the aromatic liquid into each of the inner open ends 25a, 25'a of the air tubes 25a, 25'a must be avoided.

Figure 6:
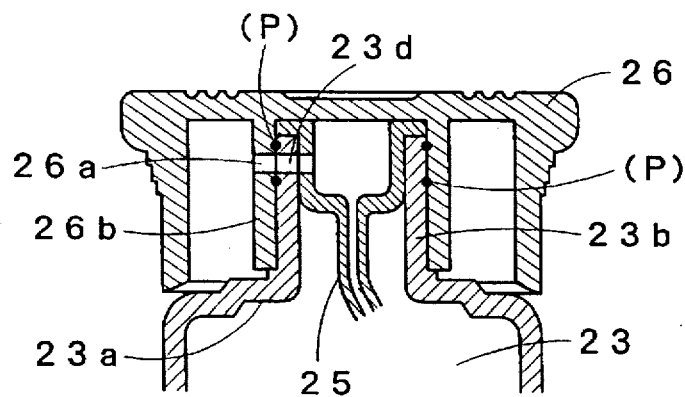
FIG. 6 is a fragmentary cross-sectional view of a lid that is engaged with the projected opening of the vessel of the device.

Lids 26, 26' fitted to the projections 23b, 24b are provided with side walls 26b, 26'b that are tightly engaged with the projections 23b, 24b as shown in the enlarged cross-sectional view in FIG. 6. The side walls 26b, 26'b have through-holes 26a, 26'a, which communicate with through-holes 23d, 24d, respectively within a certain angle of rotation margin. In view of air-tightness with the lid fully closed, appropriate gasket members (P) such as O-rings are preferably arranged to seal through-holes 23a, 26a in the projection 23b and the side wall 26b of the inner sleeve of the lid 26, with one member above and the other below the through-holes 23a, 26a. Optionally, a taper engagement may be introduced between the side wall 26b and the projection 23b in addition to the use of the gasket members (P).

The aroma emission device in the preceding two embodiments are different from the first embodiment in that the above two embodiments employ lids 16, 16' and 26, 26'. The advantage of the lids 16, 16' of thread type in the former embodiment is that the degree of tightness of the lids 16, 16' with the projections 13b, 14b opens or close the passage above the top end of the projections and the gap between both the threads of the projections 13b, 14b and the lids 16, 16' and thus controls the flow of air that is let in through the air tubes 15, 15' into the upper and lower compartments 13, 14. The advantage of the lids 26, 26' of through-hole type in the latter embodiment is that the lids 26, 26' are turned by an appropriate angle to set appropriately the size of the overall aperture of the through-holes 23d, 24d and 26a, 26'a in the projections 23b, 24b, and the lids 26, 26' to control the flow of air taken in into each compartments through the air tubes 25, 25'.

In both embodiments, during use, the upper and lower lids are properly loosened or turned to allow the through-holes to communicate, and aroma is emitted for a certain period of time in the same way as the first embodiment. To suspend emission of aroma, either the upper lid or lower lid closed. While the device is not used, both lids are fully closed. With both lids fully closed, even a highly volatile aromatic liquid is completely sealed. Liquids (K) and (K') are prevented from evaporating and thus, an economic aroma emission is assured.

Referring to the lids 16, 26 in FIGS. 3, 4 and 6, the lids for the upper compartment of the vessel have been discussed. The lids 16', 26' fully identical to the lids 16, 26 are fitted to the lower compartment as well. The adjustment means for adjusting the air taken between the projection and lid in each of the upper and lower compartments shown in the figures are interchangeably used in the vessels. Other structures may be acceptable as long as they achieve the purpose of the above embodiments.

The device of the present invention emits aroma without using any form of energy such as gas or electricity. The structure of the vessel is not limited to the description and drawings of the above embodiments, and a diversity of design changes are contemplated. For example, the vessel is not limited to a cylindrical shape. The vessel may be of a triangular form or a polygonal form or an indefinite hollow configuration. The air tubes are not limited to a straight tube (as in FIGS. 1 and 2). The air tubes may be spiral, zigzag (as in FIG. 5) or in any other form.

Symmetry between the upper and lower compartments is not a requirement as long as the level of the aromatic liquid (K) is kept below the inner open ends of the air tubes in the upper and lower compartments in the vessel 1.

As described above, the device of the present invention emits aroma out of the vessel for a certain period of time at a uniform aromatic level simply by placing the vessel upside down. By adjusting the lids fitted to the end openings at the top and bottom covering portions of the upper and lower compartments to control air flow, the emission time of aroma is freely set. Thus, the device may be used as a water clock in a hourglass fashion. In the design of the device, the vessel 1 may be formed of a transparent material for a user to see the state of transfer of the aromatic liquid between the upper and lower compartments, while coloring the aromatic liquid. Thus, aesthetic appearance and design of the vessel may be enhanced. The device may be aesthetically and conveniently placed in the interior of a room.

In the aroma emission device of the present invention, the vessel is placed upside down to emit aroma without using any energy. The device emits aroma for a certain period of time, and then stops itself. The aromatic liquid is used in an economically efficient fashion with no consumption in vain.

The aroma emission device of the present invention is useful not only for aromatic liquids such as perfumes and eau de Cologne, and deodorants, but also for medical fluids used for a diversity of aroma therapy.

What is claimed is:

1. An aroma emission device comprising a vessel that is partitioned into an upper compartment and a lower compartment, said upper and lower compartments having a top cover portion and a bottom cover portion, respectively, each of the cover portions has an air tube penetrating therethrough for communicating with the outside, the inner open end of each air tube is positioned near a partitioning plate between both compartments, and a perforation is arranged in the partitioning plate to allow the upper and lower compartments to communicate with each other.

2. An aroma emission device according to claim 1, wherein a hollow projection extends from each of the top cover portion and bottom cover portion of the upper and lower compartments of the vessel, and a lid is fitted to each hollow projection.

3. An aroma emission device according to claim 2, wherein the lid is fitted to the projection of the vessel in a screw engagement.

4. An aroma emission device according to claim 2, wherein the lid fitted to the projection of the vessel is rotatable within a predetermined angle of rotation so that a through-hole formed in the side wall of the lid and a through-hole formed in the projection are aligned for opening or closing the communication therebetween.

* * * * *